United States Patent [19]

Bradstreet et al.

[11] 4,217,901
[45] Aug. 19, 1980

[54] CRUSH-RESISTANT ADHESIVELY-ATTACHED ABSORBENT PRODUCT

[75] Inventors: James A. Bradstreet, Colts Neck; Judith E. Roller, North Brunswick, both of N.J.

[73] Assignee: Personal Products Company, Milltown, N.J.

[21] Appl. No.: 949,333

[22] Filed: Oct. 6, 1978

[51] Int. Cl.² .............................................. A61F 13/16
[52] U.S. Cl. ........................ 128/290 R; 128/DIG. 30
[58] Field of Search ............... 128/284, 285, 287, 290, 128/296, DIG. 30

[56] References Cited

U.S. PATENT DOCUMENTS

| | | | |
|---|---|---|---|
| 3,017,304 | 1/1962 | Burgeni | 128/290 R |
| 3,888,255 | 6/1975 | Shah et al. | 128/290 H |
| 3,889,678 | 6/1975 | Chatterjee et al. | 128/290 R |
| 3,971,379 | 7/1976 | Chatterjee | 128/290 P |
| 4,023,571 | 5/1977 | Comerford et al. | 128/290 P |
| 4,103,062 | 7/1978 | Aberson et al. | 128/296 |
| 4,105,033 | 8/1978 | Chatterjee et al. | 128/296 |

Primary Examiner—C. Fred Rosenbaum
Attorney, Agent, or Firm—Jason Lipow

[57] ABSTRACT

A thin absorbent product for adhesive attachment to a wearer's garment is provided with means for resisting deformation when worn or applied. Such means comprise providing on the garment facing major surface of the absorbent pad of such product, a densified, compacted, porous, absorbent, fibrous layer having a particulate hydrocolloid material distributed therein. Said densified layer provides the product with planar crush resistance.

7 Claims, 4 Drawing Figures

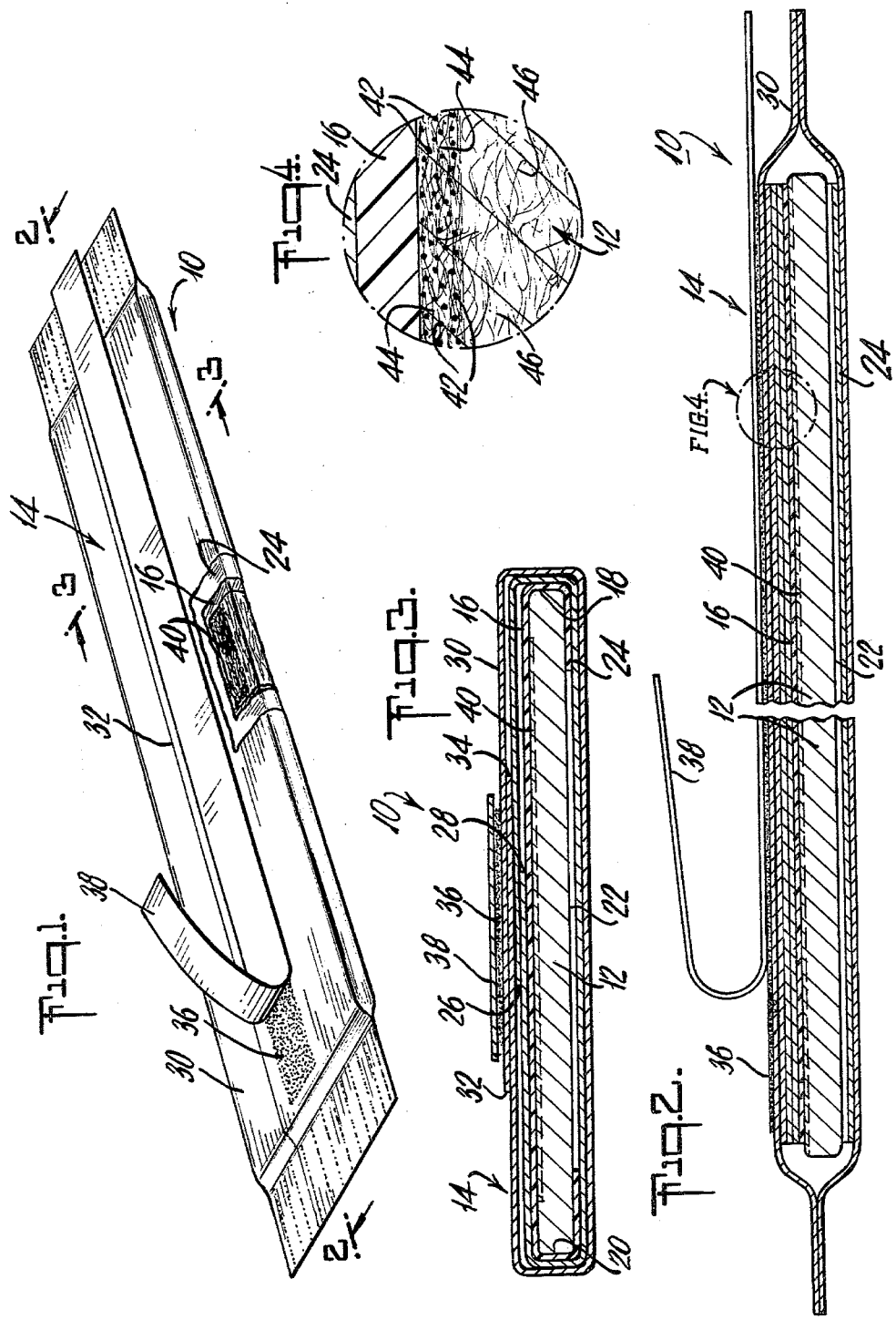

CRUSH-RESISTANT ADHESIVELY-ATTACHED ABSORBENT PRODUCT

BACKGROUND OF THE INVENTION

This invention relates in general to products for absorbing body exudate, of the kind which are retained in place by adhesive adherent to a garment. More specifically, the invention relates to such products designed to absorb vaginal discharges and to be worn by adhering to the crotch portion of an undergarment such as a panty or girdle.

The art is now replete with various suggestions for adhesively-attached sanitary napkins. Such products generally consist of an absorbent element which is optimally enclosed in a cover or cover material and provided with a pressure-sensitive adhesive element for adhering the product to the undergarment of the user. Generally, the adhesive element is provided with a removable, protective strip to protect the adhesive element prior to use. Recent emphasis has been placed on reducing the thickness of such products so that they can be comfortably worn, yet still serve their absorbent function, at least during times of light discharge such as at the beginning or end of a menstrual period, in conjunction with a catamenial tampon or even intermenstrually. Examples of such thin, adhesively-attached products are illustrated in U.S. Pat. Nos. 4,023,570 and 4,023,571.

Unfortunately, the trend toward such thin, adhesively-attached products has resulted in some concomitant drawbacks. The thinness has resulted in depriving the product of resistance to twisting, folding or crushing when being applied or in use. Accordingly, when the protective strip overlying the adhesive element is removed from the pressure-sensitive adhesive, unless the user is extremely careful, it is possible that different sections of the pressure-sensitive adhesive will adhere to one another, oftentimes causing permanent creasing or wrinkling of the product and occasionally rendering the product unusable. This problem is aggravated by the fact that the exposed, pressure-sensitive adhesive must be readily adhereable to the garment of the wearer so that, of necessity, the pressure-sensitive adhesive must be aggressively tacky. As a result, when different sections of the pressure-sensitive adhesive stick to one another, they are extremely difficult to pull apart.

In addition to the problem associated with applying such products, the thin, adhesive products exhibit a similar problem in use. When worn, these extremely flexible products tend to twist or "rope" together under the action of body movements and particularly by virtue of thigh movements so that the area presented against the body is substantially reduced and hence the protection afforded is lessened.

The above-described problems have, to a degree, been addressed in U.S. Pat. No. 3,913,580, issued on Oct. 21, 1975 to J. A. Ginocchio. As described in this patent, the adhesively-attached product is of the type having an impervious outer cover adhered to an absorbent body. The portion of the cover underlying the pressure-sensitive adhesive element is stiffened by application of a band of adhesive which also serves, together with other applied adhesive, to affix the impervious cover to the absorbent body. While such a solution works well in the relatively thick product having the specific construction described in this patent, it is, unfortunately, a less effective solution when applied to the thinner products of the various constructions considered herein. Accordingly, there is a need, in a thin, absorbent, adhesive product for means for increasing its resistance to certain kinds of deformation. Such means should be provided without effecting the primary function of the product, namely to absorb body fluids.

SUMMARY OF THE INVENTION

In accordance with this invention, a thin, absorbent product for adhesive attachment to a wearer's garment is provided with means for resisting deformation under the action of body movements when worn and for resisting unintended bending, twisting and folding when applied. The resistance to such deformation is related to the resistance of the product to a crushing force applied upon the longitudinal, edges of the product and is herein characterized as "crush resistance" and quantified by methods described below.

More specifically, the thin, absorbent, adhesively-attached product of this invention comprises a planar, generally rectangular, absorbent pad having a body-facing major surface, a garment-facing major surface, longitudinal sides and transverse ends. An outer cover is provided overlying at least the garment-facing major surface and preferably enveloping the entire pad. At least one pressure-sensitive adhesive element is disposed on the outer cover for adhering the product to a wearer's garment. Preferably one or more of the pressure-sensitive adhesive elements extend longitudinally, are centrally located on the outer cover and are protected, prior to use, by a peelably removable, protective strip.

In accordance with this invention, means are provided for endowing the pad with planar crush resistance, said means comprising providing, on the garment-facing major surface of the pad and integral therewith, a densified, compacted, porous, absorbent, fibrous layer having a particulate hydrocolloid material distributed therein. Such a densified layer may be made, for example, in accordance with methods described in U.S. Pat. No. 4,103,062, in whch a densified layer containing hydrocolloid particles is made, in situ, from a pad of absorbent fibers. As is taught by this patent, such a layer is useful to enhance the fluid retentivity of an absorbent pad. It has now been discovered that such a layer, provided on the garment-contacting side of an absorbent pad and incorporated in a thin, adhesively attached product of this invention, endows the product with substantial planar crush resistance and overcomes the difficulties heretofore associated with the undesirable twisting and creasing of these thin products.

BRIEF DESCRIPTION OF THE DRAWINGS

FIG. 1 is a perspective view of the thin, absorbent, adhesively-attached product of this invention, illustrated with the protective strip partially folded back and portions removed to expose underlying portions;

FIG. 2 is a longitudinal, cross-sectional view of the product illustrated in FIG. 1 and taken along line 2—2.

FIG. 3 is a transverse, cross-sectional view of the product illustrated in FIG. 1 and taken along line 3—3;

FIG. 4 is an enlarged, longitudinal, cross-sectional view of the portion of the product of FIG. 1 illustrating the interface between the impervious cover and the pad thereof.

DETAILED DESCRIPTION OF THE PREFERRED EMBODIMENTS

While this invention is susceptible of embodiment in many different forms, there is shown in the drawings and will herein be described in detail, a preferred embodiment of the invention with the understanding that the present disclosure is to be considered as an exemplification of the principles of the invention and is not intended to limit the invention to this illustrative embodiment.

Referring to the drawings, FIGS. 1-3 illustrate, in perspective, longitudinal, cross-sectional and transverse, cross-sectional views, respectively, a thin, absorbent, adhesively-attached product 10 embodying the teachings of this invention. As illustrated in the drawings, the major surface intended for placement against the garment is the upwardly facing surface, with the opposite, downwardly facing surface being intended for placement against the body.

The product 10 comprises a planar, generally rectangular, absorbent pad 12 which may be made up of any suitable absorbent material such as, for example, comminuted woodpulp fibers, cotton linters, rayon fibers, cotton staple and the like. Overlying the garment-facing major surface 14 of absorbent pad 12 is a body fluid impervious cover 16, provided to preclude absorbed body fluid from striking through the outermost garment-facing surface of the product and wetting or staining the undergarment. In the embodiment illustrated in the drawings, this impervious cover 16 preferably extends beyond the garment-facing surface of the pad 12 to also cover the longitudinal sides 18 and 20 of the pad as well as longitudinal, peripheral portions of the body facing surface 22 of the pad.

A generally rectangular sheet of tissue paper 24 surrounds the pad and impervious cover sub-assembly, and the longitudinal edges 26 and 28 of the tissue paper overlap onto the garment-facing surface of the sub-assembly. This tissue paper is provided to hold the sub-assembly together and hence to facilitate the further processing of the product.

The tissue-paper-wrapped sub-assembly is enveloped in a generally rectangular, body fluid pervious cover 30 which is somewhat larger than pad 12 and somewhat wider than the transverse, cross-sectional periphery of pad 12. The longitudinal edges 32 and 34 overlap on the garment-facing major surface of the product. The cover 30 may be of any of the commonly used absorbent product covers such as gauze, non-woven material reinforced with adhesive binders, and the like.

An adhesive element 36 overlies a portion of the external, garment-facing surface of cover 30 for attaching the absorbent product to an undergarment. As illustrated in the exemplary embodiment, this adhesive element comprises an elongated band of pressure-sensitive adhesive material. This material can be any of a large number of such pressure-sensitive adhesives available on the market, including the so-called cold, pressure-sensitive adhesive such as the acrylate adhesives, for example, vinyl acetate-1 ethylhexylacrylate copolymer which is generally combined with tackifiers, e.g., ethylene amine. Alternatively, the adhesive may comprise the rapid-setting thermoplastic (hot melt) adhesives such as block copolymers exemplified by styrene and butadiene copolymers. The adhesive band may also comprise a two-sided adhesive tape such as is disclosed in U.S. Pat. No. 3,643,662, issued in February, 1972, to Mary H. McGuire et al.

The adhesive element 36 is protected by a peelable, protective strip 38, illustrated in the drawings in a partially peeled off position, and provided to protect the adhesive during storage and handling prior to use. The protective strip 38 may be constructed of a relatively stiff paper that has been treated so as to be readily releasable from the adhesive element 36, e.g., as with silicone treatment.

The absorbent products 10 of this invention are contemplated as being extremely thin and, in the absence of employing means to otherwise preclude this, are extremely flexible. For example, most full-size catamenial napkins are in the order of 12.5 to 19.0 millimeter in thickness, the products of this invention are instead from about 3.0 to 7.0 millimeters thick and preferably from 4.0 to 6.0 millimeters in thickness. As noted, such extremely thin napkins tend to twist, crease or otherwise deform in an undesirable manner when applied or when worn. In accordance with this invention, means have been provided for precluding this and endowing the product with crush resistance, said means comprising providing, on the garment-facing surface of the pad 12, a densified, compacted, porous, absorbent, fibrous layer 40 having particulate hydrocolloid material distributed therein.

The densified layer 40 is contemplated as extending longitudinally and centrally on the garment-facing surface of the pad 12 and occupies a major portion of the area of this surface. As illustrated in the drawings, the layer 40 does not extend totally over the entire surface but instead falls short of the two longitudinal, peripheral areas of the pad. This is preferred in that the employment of a densified layer 30 greatly increases the wicking rate along the surface on which it is applied; i.e., the rate at which fluid striking one portion of the pad will be transported to another portion. While it is desirable to have body fluid striking a central portion of the pad wick toward the more remote portions in order to more fully utilize the total absorbent capacity of the pad, it has been discovered that it is further desirable to have such fast wicking properties fall short of the peripheral, longitudinal portion of the pad. This is because such pads fail in use when the peripheral portions become wet with body fluid. Rapid wicking, carried out to the peripheral portions, has been found to detrimentally accelerate such failure and hence is undesirable. Additionally, by confining the layer 40 to the central portion of the garment-facing surface of pad 12, the peripheral, longitudinal edges of the pad remain soft and hence the product is more comfortable when worn. Preferably then, the layer 40 occupies a minimum of about 50% of the surface area of the pad and still more preferably about 80%.

While it is preferable to limit the coverage of layer 40 to only a portion of the pad, it will be understood that the advantages of endowing the pad with crush resistance, in accordance with the teachings herein, can be accomplished by densified layers of this invention which occupy the full surface of the pad and particular circumstances, arising from the design of a given product, may make such full coverage necessary or desirable. For example, an extremely thin pad may necessitate full coverage in order to best obtain crush resistance. Further, the economics of manufacturing such products may dictate the need and desirability of full coverage.

The densified layer 40 of this invention comprises two components: a fibrous component and a hydrocolloid particle component. The fibrous component may comprise fibers of such cellulosic materials or regenerated cellulosic materials as woodpulp, cotton, cotton linters, rayon or the like. Additionally, the fibrous portion may comprise synthetic fibers such as nylon or cellulose acetate fibers. Preferably when such synthetic fibers are employed, they are employed in combination with cellulosic materials or regenerated cellulosics and not more than to the extent of about 50% by weight of the fibrous component of the layer. When the layer is to be manufactured, in situ, with the pad 12, as will be described herein, it is preferred that the fibrous portion of the layer comprise the same materials as the pad; i.e., an absorbent pad 12 comprising woodpulp, rayon, or cotton linters would preferably have a densified layer 40 comprising, as the fibrous component, these same materials.

The hydrocolloid particle component of the densified layer consists of particles of water insoluble but water swellable polymeric substances capable of absorbing water in an amount which is at least ten times the weight of the hydrocolloid particles in the dry form and is preferably about 15 to 70 times the dry weight or more.

Such material may be described chemically as having a backbone of natural or synthetic polymers with hydrophilic groups or polymers containing hydrophilic groups chemically bonded thereto or in intimate admixture therewith. Included in this class of material are such modified natural and regenerated polymers such as polysaccharides including, for example, cellulose and starch and regenerated cellulose, which are modified by being carboxy alkylated, phosphonoalkylated, sulphoalkylated, or phosphorylated to render them highly hydrophilic. Such modified polymers may also be crosslinked to enhance their hydrophilicity and render them water insoluble.

These same polysaccharides may also serve, for example, as the backbone onto which other polymer moieties may be bonded by graft copolymerization techniques. Such grafted polysaccharides and their method of manufacture are described in U.S. Pat. No. 4,105,033 issued on Aug. 8, 1978 to P. K. Chatterjee et al. and may be described as polysaccharide chains having grafted thereon a hydrophilic chain of the general formula

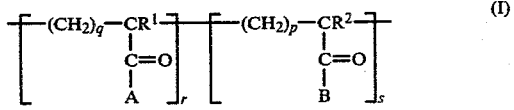

(I)

wherein A and B are selected from the group consisting of —OR$^3$, —O(alkali metal), —OHNH$_3$, —NH$_2$, wherein R$^1$, R$^2$ and R$^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1 and q is an integer having a value of 1 to 4.

The preferred hydrophilic chains are hydrolyzed polyacrylonitrile chains and copolymers of polyacrylamide and sodium polyacrylate.

In addition to modified natural and regenerated polymers, the hydrocolloid particle component of the densified layer of this invention may comprise wholly synthetic hydrophilic particles. Examples of those now known in the art are polyacrylonitrile fibers which may be modified by grafting such moieties thereon such as polyvinyl alcohol chains, polyvinyl alcohol itself, hydrophilic polyurethane, poly(alkyl phosphonates) partially hydrolyzed poly acrylamides (e.g., poly(N-N-Dimethyl acrylamide), sulfonated polystyrene, or poly(alkylene oxide). These highly hydrophilic synthetic polymers may be modified by other chemical treatments such as crosslinking or hydrolysis.

The hydrocolloid particles may take various physical shapes such as powders, fibers or flakes. Specific examples are fibers or carboxyalkylated cellulose, powders of carboxylalkylated starch or ground fibers of the grafted polysaccharides described in the aforementioned U.S. Pat. No. 4,105,033.

FIG. 4 of the drawings illustrates, in enlarged cross-sectional view, a portion of the pad 12, the densified layer 40, integal therewith, and the impervious cover 16. The layer 40 may be formed by methods described in the aforementioned U.S. Pat. No. 4,103,062 or in U.S. Pat. Nos. 2,905,568, 2,955,641 and 3,017,304 issued to A. Burgeni. Common to these methods is the air laying of a web of material and the densification of the web by means of the action of water and pressure.

In applying these methods to the invention described herein, the densified layer is formed by airlaying onto the pad 12 a mixture of the two densified layer components, i.e., the fibrous component and the hydrocolloid particle component. Preferably the hydrocolloid component is about 5.0 to about 50.0% by weight of the mixture and more preferably about 10.0 to about 25.0% by weight. While the air laid web which is comprised of these two components and will ultimately become the densified layer may be different and independent from the pad 12, it is preferred that the pad 12 itself is no more than an air-laid mixture of the two components of which the layer 40 is comprised. In this circumstance no separate and independent step is needed prior to densifying the surface of the pad to form layer 40, and the pad as a whole is rendered more absorbent by virtue of the presence of the highly hydrophilic hydrocolloid particles.

The densification may be carried out by the so-called water induced method described in the aforementioned patents to Burgeni. According to this method a controlled amount of water or an aqueous binder solution (between 0.0005 gms./cm.$^2$ and 0.03 gms./cm.$^2$) can be applied to the surface of the pad on which the densified layer 40 is desired. This surface is then subjected to a compacting pressure of between 5 psi and 100 psi (0.352 to 7.031 kg/cm$^2$) to produce the densified layer 40. Suitable compression means for this purpose may comprise a pair of platens, calender rolls, or other means.

Still another method of forming a densified layer 40 may be that described in the aforementioned U.S. Pat. No. 4,103,062 which can be characterized as a heat induced method. In accordance with this latter method, the layer is formed, not by adding water to the surface of the pad, but instead by utilizing the moisture present therein under ordinary ambient conditions. This method therefore subjects the pad to pressure simultaneously applied to both the surface on which the densified layer is to be found and to the surface opposite thereto. A temperature differential is simultaneously imposed across the pad with the surface on which the densified layer is to be formed being maintained, during or before the compression step, at a lower temperature than the opposite surface. The effect of the temperature differential is to induce the migration of the inherently present moisture away from the hot surface and toward the cold surface. There the presence of induced moisture and pressure effect the densification of the fibers to produce the layer 40 suitable for use in accordance with this invention. A temperature differential of at least about 40 Fahrenheit degrees (22.2 Centigrade degrees) or higher is suitable and the pad should be subjected to a pressure differential of at least 2 and preferably about 4 to about 15 kg/cm$^2$.

In accordance with the teachings of this invention, the adhesively attached products incorporating the densified layers as defined herein are endowed with substantially increased planar crush resistance. Such crush resistance is related to the ability of the product to withstand a force exerted on the longitudinal edges of the pad and is quantified by the following test.

A sample of the product has the protective strip removed and is rolled into a cylinder by overlapping the transverse ends of the product to form a hollow cylinder. The product is maintained in this position by adhering the overlapped ends using the pressure sensitive adhesive element. The cylinder is then compressed in an Instron Tester at a crosshead speed of 10 inches per minute. The Tester is provided with a recorder adopted to provide a stress/strain curve. Crush resistance is the force measurement recorded at the first inflection point of the stress/strain curve. Typically, by applying the teachings of this invention, such crush resistance values as from about 1.0 to about 3.0 pounds per square inch are obtained.

EXAMPLE

A series of thin, adhesively attached, absorbent products, having the construction illustrated in the drawings, are prepared. Each product comprises an absorbent pad having a length of 7.5 inches, a width of 2.5 inches and a thickness of 0.24 inches. The pads are enveloped in a non-woven cover and provided with an impervious barrier consisting of a sheet of polyethylene having a thickness of 1 mil. A hot melt pressure sensitive adhesive is applied in a single longitudinal band on the garment facing surface of the product. The overall length of the enveloped product is 9 inches. The absorbent material of the pad consists of 3.8 grams of bleached, southern pine wood pulp.

A second series of products is made, each of which products is identical to those of the first series with the exception that the absorbent pad consists of a homogeneous admixture of 3.3 grams of the aforementioned wood pulp and 0.5 grams of wood pulp which has been carboxymethylated to a degree of substitution of about 0.7 carboxymethyl groups per anhydroglucose unit and then crosslinked to render such material hydrophilic and water insoluble. Such material has been obtained from Hercules Inc. of Wilmington, Del. and sold by them under the tradename Aqualon C.

Each of the two series of pads has the garment facing surfaces thereof treated by spraying onto the surface 0.01033 grams per centimeter of water and subjecting the surface to a compression force of about 20 psi to form a densified layer thereon.

The samples are then tested in accordance with the method described above to determine their crush resistance. The Table below indicates the results.

| Sample Description | Crush Resistance (lbs. per square inch) | |
|---|---|---|
| | Average | Range |
| Pad with untreated pulp only | 0.50 | 0.372 to 0.556 |
| Pad with untreated pulp and carboxymethylated cellulose | 2.06 | 1.89 to 2.11 |

As can be seen from the above table, while both types of samples were provided with densified layers, it is only the sample incorporating the densified layer having both a fibrous component and a hydrocolloid component which exhibits substantial crush resistance.

What is claimed is:

1. A thin catamenial absorbent product for adhesive attachment to a wearer's garment comprising:
   a planar, generally rectangular, absorbent pad having a body-facing major surface and a garment-facing major surface;
   an outer cover overlying at least the garment-facing major surface;
   a pressure-sensitive adhesive element disposed on said outer cover for adhering said product to a wearer's garment; and
   means for providing said pad with planar crush resistance, said means comprising providing on said garment-facing major surface of the pad and integral therewith, a densified, compacted, porous, absorbent, fibrous layer having a particulate hydrocolloid material distributed therein;
   said hydrocolloid material being capable of absorbing water in an amount which is at least 10 times its own weight in dry form and comprising not more than 50% by weight of said densified layer; said product having a thickness of from about 3.0 to about 7.0 millimeters and having a crush resistance of from about 1.0 to about 3.0 pounds per square inch.

2. The absorbent product of claim 1 having a thickness of from about 4.0 to about 6.0 millimeters.

3. The absorbent product of claim 1 wherein the hydrocolloid material is chosen from the group consisting of carboxyalkylated, phosphonoalkylated, sulphoalkylated and phosphorylated polysaccharides.

4. The absorbent product of claim 1 wherein the hydrocolloid material comprises a grafted polysaccharide, said grafted polysaccharide consisting of a cellulose backbone having grafted thereon hydrophillic chains having the formula

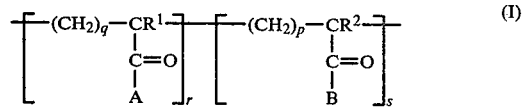

wherein A and B are selected from the group consisting of —OR$^3$, —O(alkali metal), —OHNH$_3$, —NH$_2$, wherein R$^1$ and R$^2$ and R$^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1 and q is an integer having a value of 1 to 4.

5. The absorbent product of claim 1 wherein said densified layer overlies the entire garment facing surface of said absorbent pad.

6. The absorbent product of claim 1 wherein said densified layer is centrally located on the garment facing surface of said pad and extends toward the longitudinal peripheral portions of said surface to the degree that said densified layer overlies at least 50% of said garment facing surface of said pad.

7. The absorbent product of claim 1 wherein said pad and said densified layer both comprise a fibrous portion and a particulate hydrocolloid portion.

* * * * *

REEXAMINATION CERTIFICATE (2926th)

United States Patent [19]
Bradstreet et al.

[11] B1 4,217,901
[45] Certificate Issued Jun. 25, 1996

[54] CRUSH-RESISTANT ADHESIVELY-ATTACHED ABSORBENT PRODUCT

[75] Inventors: James A. Bradstreet, Colts Neck; Judith E. Roller, North Brunswick, both of N.J.

[73] Assignee: McNeil-PPC, Inc.

Reexamination Requests:
No. 90/002,327, Apr. 23, 1991
No. 90/002,443, Sep. 18, 1991
No. 90/002,763, Jun. 29, 1992
No. 90/002,832, Sep. 11, 1992

Reexamination Certificate for:
Patent No.: 4,217,901
Issued: Aug. 19, 1980
Appl. No.: 949,333
Filed: Oct. 6, 1978

[51] Int. Cl.$^6$ .......................... A61F 13/16; A61F 13/15
[52] U.S. Cl. .......................... 604/368; 604/378; 604/387; 604/366; 604/371; D24/124
[58] Field of Search .......................... 604/368, 385.1, 604/385.2, 370

[56] References Cited

U.S. PATENT DOCUMENTS 3,938,522  2/1976  Repke .......................... 128/287
4,232,674  11/1980  Melican .
4,252,761  2/1981  Schoggen .......................... 264/120

FOREIGN PATENT DOCUMENTS 52-44155  11/1977  Japan .

OTHER PUBLICATIONS

"Cross–linked Derivative (CLD) Fibers as Binders for Non-–Wovens" Walter L. Dean Mar. 6, 1974 INDA.

"Improved Absortive Pads Using Consolidated Forms of Superabsorbent Materials".

"Absorbent Starch Based Copolymers—Their Characteristics and Applications" Lindsay—Formed Fabrics Ind.

*Primary Examiner*—Robert Clark

[57] ABSTRACT

A thin absorbent product for adhesive attachment to a wearer's garment is provided with means for resisting deformation when worn or applied. Such means comprise providing on the garment facing major surface of the absorbent pad of such product, a densified, compacted, porous, absorbent, fibrous layer having a particulate hydrocolloid material distributed therein. Said densified layer provides the product with planar crush resistance.

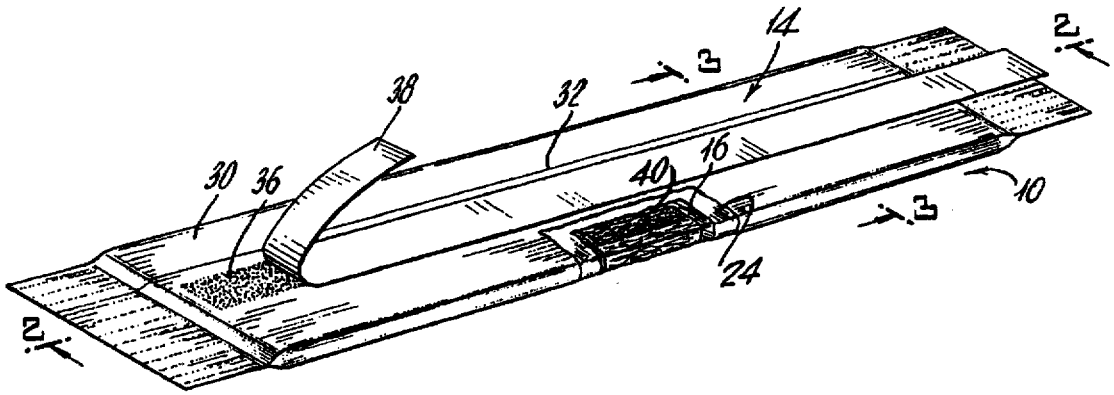

B1 4,217,901

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–7 are cancelled.

New claims 8–15 are added and determined to be patentable.

8. *A thin catamenial absorbent product for adhesive attachment to a wearer's garment comprising:*

*a planar, generally rectangular, absorbent pad having a body-facing major surface and a garment-facing major surface;*

*an outer cover overlying at least the garment facing major surface;*

*a pressure-sensitive adhesive element disposed on said outer cover for adhering said product to a wearer's garment; and*

*means for providing said pad with planar crush resistance, said means comprising providing on said garment-facing major surface of the pad and integral therewith, a densified, compacted, porous, absorbent, fibrous layer having a particulate hydrocolloid material distributed therein, wherein said layer is different from said absorbent pad;*

*said hydrocolloid material being capable of absorbing water in an amount which is at least 10 times its own weight in dry form and comprising not more than 50% by weight of said densified layer; said product having a thickness of from about 3.0 to about 7.0 millimeters and having a crush resistance of from about 1.0 to about 3.0 pounds per square inch.*

9. *A product of claim 8 wherein said product has a crush resistance of from about 1.0 to about 2.0 pounds per square inch.*

10. *A product of claim 8 wherein said fibrous portion of said densified, compacted, porous, absorbent, fibrous layer consists essentially of wood pulp fiber.*

11. *A product of claim 9 wherein said fibrous portion of said densified, compacted, porous, absorbent, fibrous layer consists essentially of wood pulp fiber.*

12. *A thin catamenial absorbent product for adhesive attachment to a wearer's garment comprising:*

*a planar, generally rectangular, absorbent pad having a body-facing major surface and a garment-facing major surface;*

*an outer cover overlying at least the garment facing major surface;*

*a pressure-sensitive adhesive element disposed on said outer cover for adhering said product to a wearer's garment; and*

*a densified, compacted, porous, absorbent, fibrous layer having a particulate hydrocolloid material distributed therein, which layer provides said pad with planar crush resistance, said layer being different from said absorbent pad and being provided on said garment-facing major surface of the pad and integral therewith;*

*said hydrocolloid material being capable of absorbing water in an amount which is at least 10 times its own weight in dry form and comprising not more than 50% by weight of said densified layer; said product having a thickness of from about 3.0 to about 7.0 millimeters and having a crush resistance of from about 1.0 to about 3.0 pounds per square inch.*

13. *A product of claim 12 wherein said product has a crush resistance of from about 1.0 to about 2.0 pounds per square inch.*

14. *A product of claim 12 wherein said fibrous portion of said densified, compacted, porous absorbent, fibrous layer consists essentially of wood pulp fiber.*

15. *A product of claim 13 wherein said fibrous portion of said densified, compacted, porous, absorbent, fibrous layer consists essentially of wood pulp fiber.*

\* \* \* \* \*